United States Patent
Yoshida et al.

(10) Patent No.: US 11,002,748 B2
(45) Date of Patent: May 11, 2021

(54) ANALYZING DEVICE MANAGEMENT SYSTEM

(71) Applicant: SHIMADZU CORPORATION, Kyoto (JP)

(72) Inventors: Takeshi Yoshida, Kyoto (JP); Koki Yamamoto, Kyoto (JP); Teppei Kodama, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 311 days.

(21) Appl. No.: 15/957,362

(22) Filed: Apr. 19, 2018

(65) Prior Publication Data

US 2019/0004074 A1 Jan. 3, 2019

(30) Foreign Application Priority Data

Apr. 20, 2017 (JP) .............................. JP2017-083533

(51) Int. Cl.
*G01N 35/00* (2006.01)
*G06Q 50/00* (2012.01)
(Continued)

(52) U.S. Cl.
CPC . *G01N 35/00623* (2013.01); *G01N 35/00722* (2013.01); *G01N 35/00871* (2013.01);
(Continued)

(58) Field of Classification Search
CPC ....... G01N 35/00871; G01N 35/00623; G01N 35/00722; G01N 2035/00633; G01N 2035/0091; G01N 2030/8881; G01N 30/8696; G16H 10/40; G16H 40/40; G16H 40/67; G06Q 50/00
See application file for complete search history.

(56) References Cited

U.S. PATENT DOCUMENTS 6,263,322 B1 * 7/2001 Kirkevold .......... G06Q 30/0283
705/400
6,483,292 B2 11/2002 Kochi
(Continued)

FOREIGN PATENT DOCUMENTS

| JP | 2003-344422 A | 12/2003 |
|---|---|---|
| JP | 4497257 B2 | 7/2010 |
| JP | 2011-185794 A | 9/2011 |

*Primary Examiner* — Yoshihisa Ishizuka
(74) *Attorney, Agent, or Firm* — Sughrue Mion, PLLC

(57) ABSTRACT

A system for managing modular analyzing devices 110*a-c* includes: a means 161 for acquiring the serial number of modules included in each analyzing device; a means 161 for acquiring information on an expendable part included in each module; a storage section 152 for storing the acquired serial number and expendable-part information in the state of being associated with a system controller to which the module corresponding to the serial number is connected; a transfer detector 164 for detecting a transfer of an operation module based on the serial numbers associated with each system controller; and an information manager 163 for changing the association of the expendable-part information in the storage section, from the state of being associated with the system controller on the giving end of the transfer, to the state of being associated with the system controller on the receiving end of the transfer, when the transfer is detected.

13 Claims, 8 Drawing Sheets

(51) Int. Cl.
*G16H 40/67* (2018.01)
*G16H 10/40* (2018.01)
*G16H 40/40* (2018.01)
G01N 30/86 (2006.01)
G01N 30/88 (2006.01)

(52) U.S. Cl.
CPC ............ *G06Q 50/00* (2013.01); *G16H 10/40* (2018.01); *G16H 40/40* (2018.01); *G16H 40/67* (2018.01); *G01N 30/8696* (2013.01); *G01N 2030/8881* (2013.01); *G01N 2035/0091* (2013.01); *G01N 2035/00633* (2013.01)

(56) References Cited

U.S. PATENT DOCUMENTS

| | | | | |
|---|---|---|---|---|
| 7,243,535 | B2* | 7/2007 | Shimura | B60C 23/0442 |
| | | | | 73/146.5 |
| 8,121,910 | B2* | 2/2012 | Syme | G06Q 10/0875 |
| | | | | 705/29 |
| 2001/0043063 | A1* | 11/2001 | Kochi | G01R 31/392 |
| | | | | 702/183 |
| 2006/0195283 | A1* | 8/2006 | Tokunaga | G01N 35/00871 |
| | | | | 702/105 |
| 2015/0239306 | A1* | 8/2015 | Bracq | B60C 23/0479 |
| | | | | 702/140 |

* cited by examiner

Fig. 2

| | Module Name | Model Number | Serial Number | Name of Expendable | Model Number | Number of Times of Use | Degree of Degradation |
|---|---|---|---|---|---|---|---|
| 1 | Liquid supply unit | F-46GB | a12354 | Pump seal | PS-045 | 123 | |
| 2 | | | | Piston | 678PX | 3974 | |
| 3 | Auto-sampler | AS-634X | 34983b | Needle | N-1678 | 3423 | |
| 4 | | | | Sampling loop | LP-450N | 689 | |
| 5 | Column oven | OV35X | c28997 | Heater | H234X | 34 | |
| 6 | Detector | D145S | d0001 | Lamp | L789S | 1257 | |
| 7 | | | | Flow cell | FC54N | 450 | |

Tabs: SC-1 (211), SC-2 (212), SC-3 (213)

Management Information — 210

ANALYZING DEVICE MANAGEMENT SYSTEM

TECHNICAL FIELD

The present invention relates to a management system for managing analyzing devices which perform chemical or physical analyses of samples.

BACKGROUND ART

In many cases, an analyzing device, such as a liquid chromatograph or spectrophotometer, includes so-called "expendable parts" which degrade with their use and can no longer be used after they have reached a certain degree of degradation. Examples of such expendable parts include: a seal (packing) in a liquid supply pump of a liquid chromatograph, a lamp in a light source of a spectrophotometer, a filament in an electron beam source of an electron microscope, and a cantilever in a scanning probe microscope.

Conventionally, in order to replace such expendable parts at appropriate timing, users have manually recorded the number of times of use, time of use and other items of information concerning each expendable part (such items of information are hereinafter called the "use history"). Referring to the use history, users have performed necessary tasks, such as placing an order of an expendable part or replacing it with a new one. However, such a method consumes time and labor. Furthermore, if a user does not properly record the use history or omits to refer to the use history, a degraded part may be further used without being appropriately replaced, thereby causing a problem with an analysis.

Accordingly, in recent years, systems for automatically managing use histories of such expendable parts by computers have been widely and increasingly used. For example, Patent Literature 1 discloses a system which automatically collects use histories of expendable parts from a plurality of analyzing devices and uploads the collected data onto a management server on a computer network to perform a unified management.

Some analyzing devices are constructed in the form of a so-called "modular" device composed of the combination of a plurality of modules (exchangeable structural units). For example, some of the latest liquid chromatographs (LC) are composed of modules including: a liquid supply unit for supplying an eluant (mobile phase) to a separation column; an auto-sampler including an injector for injecting a liquid sample into the eluant at a point before the column; a column oven which contains the column and controls its temperature, and a detector for detecting each sample component in an eluate from the column. Those modules (which are hereinafter called the "operation modules") are combined into a single LC (for example, see Patent Literature 2). The operation modules in such a modular type of LC are individually connected to a system controller and configured to cooperate with each other through the system controller. The system controller is connected to a personal computer (PC), which performs various tasks, such as processing data obtained from the detector or receiving a command from a user.

One advantage of constructing an analyzing device in a modular form as just described is the flexibility which allows only one operation module to be replaced with a different type (model) of module as needed according to the purpose of the analysis or other relevant factors. For example, an institution or similar organization which performs contracted analyses may have a plurality of LCs. If those LCs are constructed as modular devices in the previously described manner, it is possible to easily construct an LC including an optimum combination of the operation modules for the target sample to be analyzed, purpose of the analysis, and other relevant factors by exchanging operation modules among the LCs.

A system for automatically managing the use history of expendable parts by a computer as described earlier may also be used for such modular LCs. In an automatic management system for such modular LCs, the personal computer collects management information, which includes the configuration of the LC, use history of the expendable parts in each operation module and other items of information, from the system controller in each LC at regular intervals of time. The collected management information is stored in a storage device in the personal computer or transmitted to and stored in the server on the network. Based on the stored information, it is possible, for example, to collect time-series data showing the values of the number of times of use of each expendable part obtained from the collected use history of the expendable parts. Such time-series data allow users to easily recognize the past usage of each expendable part. Additionally, for example, based on the gradient of a graph which shows the temporal change of the number of times of use, the system can automatically predict the timing for the replacement of each expendable part and show it to the user.

CITATION LIST

Patent Literature

Patent Literature 1: JP 2003-344422 A
Patent Literature 2: JP 2011-185794 A

SUMMARY OF INVENTION

Technical Problem

In the conventional automatic management system for modular LCs mentioned earlier, only the name of the system controller in each LC and the model numbers of the operation modules connected to each system controller are collected as the information concerning the configuration of the LC among the management information. Therefore, for example, if a specific operation module in one LC has been replaced with another operation module having the same model number, the system cannot recognize the situation by itself. This causes a problem; for example, if an operation module included in one LC is transferred to another LC, the time-series data of the number of times of use of the expendable parts which have been accumulated for the operation module in the LC on the receiving end of the transfer will be replaced by the data of the number of times of use of the expendable parts of the newly transferred operation module in the middle of the data.

Although the previous description is concerned with the case of a system for managing modular LCs, the previously described problem is not limited to LCs but is common to all systems for managing modular analyzing devices.

The present invention has been developed in view of the previously described point. Its objective is to provide an analyzing device management system which can properly manage the use history of expendable parts in the operation modules of modular analyzing devices even when a transfer of an operation module is performed among those devices.

Solution to Problem

An analyzing device management system according to the present invention developed for solving the previously described problem is a system for managing a plurality of analyzing devices, each analyzing device including a plurality of operation modules and a system controller which performs a general control of the operation modules, the system including:

a) a module identifier acquiring means for repeatedly acquiring, from the system controller included in each of the analyzing devices, with a previously determined first timing, a module identifier for each of the operation modules connected to the system controller, the module identifier being unique to each of the individual products of the operation modules;

b) an expendable part information acquiring means for repeatedly acquiring, from the system controller included in each of the analyzing devices, with a previously determined second timing, information concerning a use history of an expendable part included in each of the operation modules connected to the system controller;

c) an information storing means for storing a module identifier acquired by the module identifier acquiring means, the module identifier being associated with an identifier of the system controller to which the operation module corresponding to the module identifier is connected, and for storing the information concerning a use history of an expendable part acquired by the expendable part information acquiring means, the information being associated with the identifier of the system controller to which the operation module including the expendable part is connected;

d) a module transfer detecting means for detecting a transfer of an operation module from one of the plurality of analyzing devices to another one of the plurality of analyzing devices, based on the module identifier associated with the identifier of each system controller and stored in the information storing means; and e) an information managing means for changing the association of the module identifier of a transferred operation module and the information concerning the use history of the expendable part included in the operation module, stored in the information storing means, from the state of being associated with the identifier of the system controller on the giving end of the transfer, to the state of being associated with the identifier of the system controller on the receiving end of the transfer, when the transfer of the operation module is detected by the module transfer detecting means.

The "module identifier" and "identifier of a system controller" are each a number or code which is unique to each operation module or system controller. They may typically be, but is not limited to, a serial number or production number of the operation module or system controller concerned. As another example, original names given by a user may be used.

The "information concerning a use history of an expendable part" should minimally include information on the number of times of use or time of use of the expendable part, and may additionally include use conditions or other items of information concerning the expendable part. The information storing means may store the information on the number of times of use or time of use of the expendable part in the form of an accumulated value, although it is more preferable to store the information in the form of time-series data.

The "previously determined first timing" and "previously determined second timing" may be the same timing or different timings. Each of those "timings" may be defined as a predetermined interval of time or point in time, or it may be defined as the timing of an input of a predetermined command from a user, or as the timing of an initiation or completion of a specific process by an analyzing device.

After an operation module is transferred from one analyzing device to another one, or specifically, for example, after detection unit "a" included in one LC (which is hereinafter called "LC1") is transferred to another LC (which is hereinafter called "LC2"), there is no longer any detection unit connected to the LC1 on the giving end of the transfer. However, the system controller normally cannot distinguish between the state in which a specific operation module (in the present example, the detection unit) is not connected and the state in which the operation module is connected but is not energized. Accordingly, the module identifier of the operation module which was connected until that time (in the present example, detection unit "a") is still retained in the memory of the system controller on the giving end of the transfer. Therefore, in the present situation, even after the transfer of the detector "a", the module identifier of the detector "a" is still acquired from the system controller of LC1 on the giving end of the transfer by the module identifier acquiring means in the analyzing device management system according to the present invention.

Consequently, in the information storing means, the module identifier of the detector "a" is associated with the identifier of the system controller of LC1 both before and after the transfer. Meanwhile, on the receiving end of the transfer, the module identifier of the newly connected detector "a" is stored in the memory of the system controller of LC2. Therefore, after the transfer of the detector "a", the module identifier of the detector "a" is acquired from the system controller of LC2 by the module identifier acquiring means. However, the module identifier of the detector "a" is already associated with the identifier of the system controller of LC1 in the information storing means. If this situation is not corrected, the module identifier of the detector "a" will be associated with both the system controller of LC1 and that of LC2 in the information storing means (i.e. a double registration occurs).

Consider another situation where operation modules have been exchanged between two analyzing devices. For example, consider the case where the detector "a" included in LC1 and the detector "b" included in LC2 have been exchanged. After the exchange, the module identifier of the detector "b" is stored in the memory of the system controller of LC1, while that of the detector "a" is stored in the memory of the system controller of LC2.

Therefore, when the module identifier acquiring means initially acquires the module identifier from LC1 at a later point in time, the module identifier of the detector "b" is obtained. However, at that point in time, the module identifier of the detector "b" is associated with the identifier of the system controller of LC2 in the information storing means. Accordingly, if the situation is not corrected, the double registration of the module identifier occurs.

Accordingly, the analyzing device management system according to the present invention may preferably be configured to detect the transfer of an operation module based on an occurrence of such a situation.

That is to say, the analyzing device management system according to the present invention may preferably be configured as follows: The module transfer detecting means judges that a transfer of an operation module has occurred, if the module identifier related to an operation module connected to the system controller of one of the plurality of analyzing devices is already associated with the identifier of another system controller and stored in the information storing means at the point in time where the module identifier concerned is acquired from the system controller concerned by the module identifier acquiring means.

According to this configuration, the module transfer detecting means can detect an occurrence of the transfer of an operation module by simply determining whether or not the identifiers of the operation modules acquired from one system controller by the module identifier acquiring means include a module identifier which is already associated with another system controller and stored in the information storing means. This method reduces the data-processing load, for example, as compared to the case where the presence or absence of a transfer of an operation module is determined by comparing the module identifiers newly acquired from each system controller with the module identifiers previously acquired from the same system controller.

Consider still another situation where an operation module is removed from one analyzing device and replaced by an operation module which has not been included in any of the plurality of analyzing device. For example, consider the case where the detector "a" is removed from LC1 and replaced by a new detector "x". In this case, the identifier of the detector "x" is not associated with any system controller in the information storing means. Therefore, it is impossible to detect such a transfer of the module based on the duplication of the identifier in the previously described manner.

Accordingly, the analyzing device management system according to the present invention may preferably be configured as follows:

The module transfer detecting means additionally has the function of judging that a transfer of a new operation module to the system controller has occurred in one of the plurality of analyzing devices, if the module identifier related to an operation module connected to the system controller concerned is a new module identifier which is not related to the identifier of any system controller in the information storing means at the point in time where the module identifier concerned is acquired from the system controller concerned by the module identifier acquiring means; and the information managing means additionally has the function of storing a new module identifier of a new operation module in the information storing means, if it is judged by the module transfer detecting means that a transfer of the new operation module has occurred, the new module identifier being associated with the identifier of a system controller for which it has been judged that the transfer of the new operation module has occurred.

As noted earlier, it is not always necessary to simultaneously acquire the module identifier and the information concerning the use history of an expendable part with the same timing. As one possible example, the module identifier may be acquired in a system check which is normally performed once every day (an automatic check on whether or not the analyzing device is in the normal condition), while the information concerning the use history of an expendable part may be acquired every time an operation module including the expendable part is activated, or at regular intervals of time (e.g. once every hour). However, in such a case, it is possible that, after the transfer of an operation module, the acquisition of the information concerning the use history of an expendable part by the expendable part information acquiring means is carried out earlier than the acquisition of the module identifier by the module identifier acquiring means. In that case, if the information concerning the use history is directly stored in the information storing means, an undesirable situation may occur in the information storing means, such as the situation where the number of times of use, time of use or other items of information concerning the use history of an expendable part in one operation module suddenly changes in appearance, despite the fact that there is no change in the module identifiers of the operation modules associated with the identifier of the system controller.

Accordingly, the analyzing device management system according to the present invention may preferably further include:

f) a temporary identifier assigning means for determining, at the point in time where the information concerning the use history of an expendable part included in one of the plurality of operation modules is acquired by the expendable part information acquiring means, the amount of change of the acquired information from the information concerning the use history of the same expendable part stored in the information storing means, and for associating the information concerning the use history of the expendable part at the aforementioned point in time and the subsequently obtained information concerning the use history of the expendable part with a temporary module identifier different from the module identifier of any of the operation modules and storing the information in the information storing means, if the aforementioned change is equal to or greater than a predetermined threshold, and after the operation of storing the information concerning the use history of the expendable part associated with the temporary module identifier is initiated in the information storing means, when a transfer of an operation module is detected by the module transfer detecting means, the information managing means changes the association of the information concerning the use history of the expendable part associated with the temporary module identifier and stored in the information storing means, to the state of being associated with the identifier of the system controller on the receiving end of the transfer.

This configuration prevents the situation where the information concerning the use history of an expendable part acquired within the period from a transfer of an operation module to the detection of the transfer is associated with an incorrect operation module and stored.

Advantageous Effects of the Invention

As described to this point, the analyzing device management system according to the present invention can properly manage information concerning the use history of an expendable part even when an operation module is transferred from one analyzing device to another.

BRIEF DESCRIPTION OF DRAWINGS

FIG. 2 is a diagram showing one example of a screen display in the embodiment.

DESCRIPTION OF EMBODIMENTS

The following section describes specific modes for carrying out the present invention, giving embodiments. The following description deals with an example in which a management system according to the present invention is applied in the management of modular liquid chromatographs (LCs). Needless to say, the present invention can be used as a management system for other types of modular analyzing devices (e.g. modular gas chromatographs).

EMBODIMENTS

Figure 1:
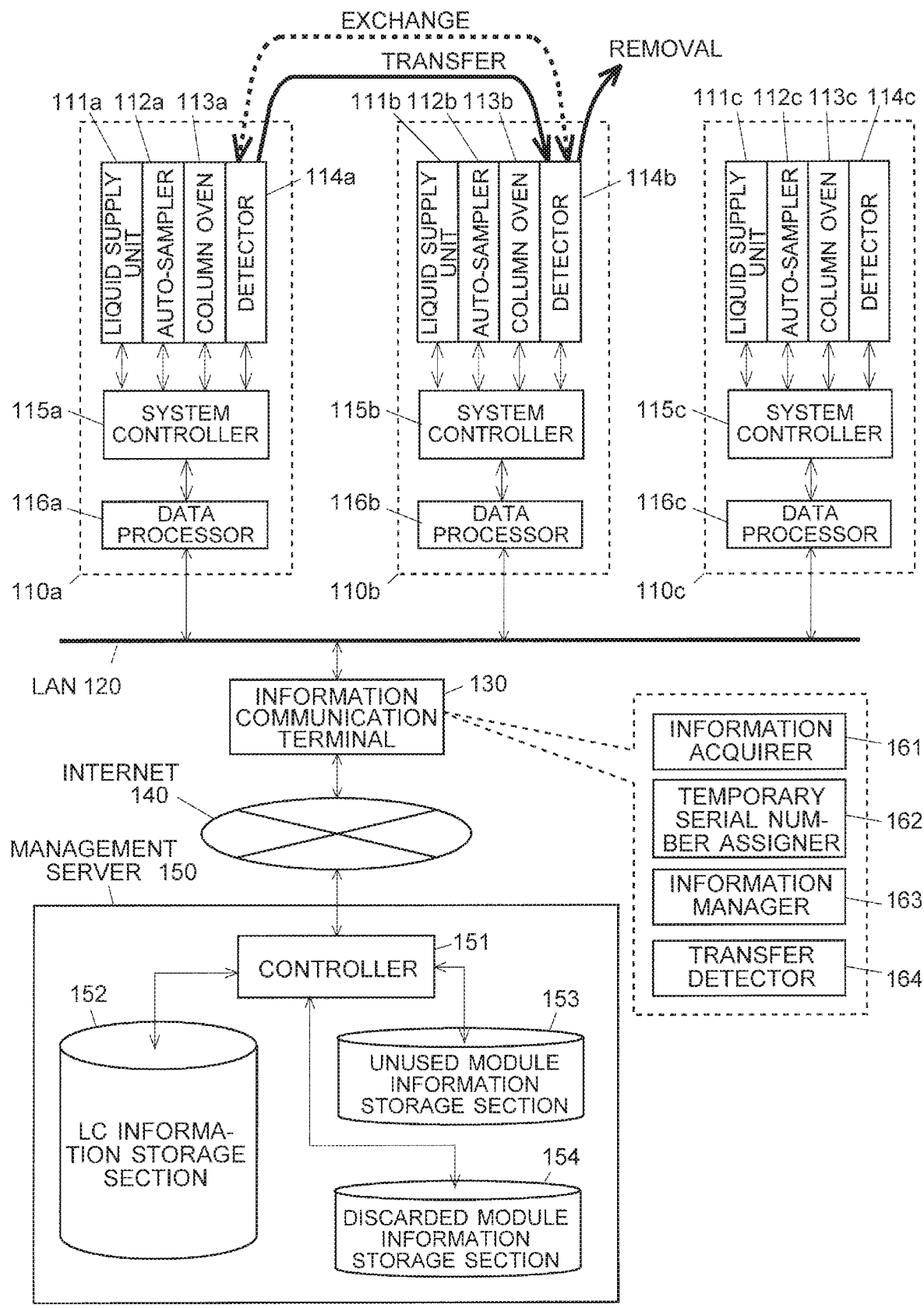
FIG. 1 is a model diagram showing an analyzing device management system according to one embodiment of the present invention.

FIG. 1 is a schematic configuration diagram of a management system for modular LCs according to one embodiment of the present invention. The management system according to the present embodiment includes an information communication terminal 130 connected to a plurality of LCs 110a-c via a local area network (LAN) 120 and a management server 150 connected to the information communication terminal 130 via the Internet 140.

Each of the LCs 110a-c includes: four operation modules, i.e. a liquid supply unit 111a-c, auto-sampler 112a-c, column oven 113a-c and detection unit 114a-c; a system controller 115a-c for performing an overall control of the operation modules; and a data processor 116a-c connected to the system controller 115a-c. The operation modules 111a-c, 112a-c, 113a-c and 114a-c as well as the system controller 115a-c each have a microcontroller and communication functions, with a predetermined control program in the microcontroller. According to this control program, the operation modules and system controller achieve predetermined functions and operations. The data processor 116a-c is a personal computer (PC) including a central processing unit (CPU), random access memory (RAM), hard disk, and other components. By executing a dedicated processing program installed on the PC, the CPU conducts predetermined waveform processing and mathematical processing on data received from the detection unit 114a-c during a sample analysis performed with the operation modules, to derive qualitative analysis results or quantitative analysis results. An operation unit (not shown) including a keyboard, mouse and other devices, as well as a display unit (not shown) including a liquid crystal display and other components, are connected to each data processor 116a-c. Watching the display unit, users can give appropriate commands to the data processor 116a-c through the operation unit.

The information communication terminal 130 is also constructed based on a PC including a CPU, RAM, hard disk and other devices. An operation unit and display unit (both not shown) similar to the aforementioned ones are also connected to the PC. Watching the display unit, users can give appropriate commands to the information communication terminal 130 through the operation unit. In FIG. 1, an information acquirer 161 (which corresponds to the "module identifier acquiring means" and "expendable part information acquiring means" in the present invention), temporary serial number assigner 162 (which corresponds to the "temporary identifier assigning means" in the present invention), information manager 163 (which corresponds to the "information managing means" in the present invention), and transfer detector 164 (which corresponds to the "module transfer detecting means" in the present invention) are shown in relation to the information communication terminal 130. They are functional blocks realized by loading a management program installed on the hard disk of the information communication terminal 130 into the RAM and executing the same program by the CPU (those functional blocks will be described later in detail).

The management server 150 is also a computer including a CPU, RAM, hard disk and other components, which is connected to the information communication terminal 130 via the Internet 140 for bidirectional data communication. The management server 150 includes a controller 151, LC information storage section 152 for storing information concerning each LC (which corresponds to the "information storing means" in the present invention), unused module information storage section 153 for storing information concerning operation modules which are not in use (i.e. which are placed in storage without being connected to any LC), and discarded module information storage section 154 for storing information concerning discarded operation modules. The storage sections 152-154 are provided on the hard disk included in the aforementioned computer functioning as the management server 150. The controller 151 is a functional means realized by loading a server program installed on the hard disk of the computer into the RAM and executing the same program by the CPU. This controller controls the reading and writing of data from and in the storage sections 152-154 as well as achieves basic management functions, such as a data search.

The LC information storage section 152 holds the following items of information associated with the identifier (e.g. a name given by a user) of the system controller 115a-c included in each of the LCs 110a-c: model numbers of a plurality of operation modules included in the LC concerned; the serial number of each operation module (which corresponds to the "module identifier" in the present invention); and information on the number of times of use or time of use of an expendable part included in each operation module (which corresponds to the "information concerning the use history of an expendable part" in the present invention). In the unused module information storage section 153, the serial number of each operation module which is placed in storage without being connected to any LC is associated with the information on the number of times of use or time of use of an expendable part included in that operation module. In the discarded module information storage section 154, the serial number of each operation module which was used in the past and has already been discarded is associated with the information on the number of times of use or time of use of an expendable part included in that operation module.

The information stored in the storage section 152-154 of the management server 150 can be read by the controller 151 and transmitted through the Internet 140 to the information communication terminal 130, to be displayed on the screen of the display unit connected to the information communication terminal 130. FIG. 2 shows one example of the display screen presented in such a case. The display screen 210 in FIG. 2 is designed to display information stored in the LC information storage section 152. The screen has tabs 211-213 which respectively correspond to the system controllers 115*a-c*. The labels "SC-1", "SC-2" and "SC-3" on those tabs indicate the names of the system controllers 115*a-c* previously given by the user (each of which corresponds to the "identifier of the system controller" in the present invention). Those names "SC-1", "SC-2" and "SC-3" are hereinafter called the "system IDs". By selecting one of those tabs on this screen, the user can refer to various items of information concerning the desired system controller, which include: the name, model number and serial number of each operation module connected to the system controller; the name and model number of each expendable part included in each operation module; and the number of times of use of each expendable part as well as its degree of degradation. The degree of degradation is shown by a bar chart indicating the ratio of the current number of times of use of each expendable part to the upper limit of the number of times of use of the same expendable part under normal conditions.

Figure 3:
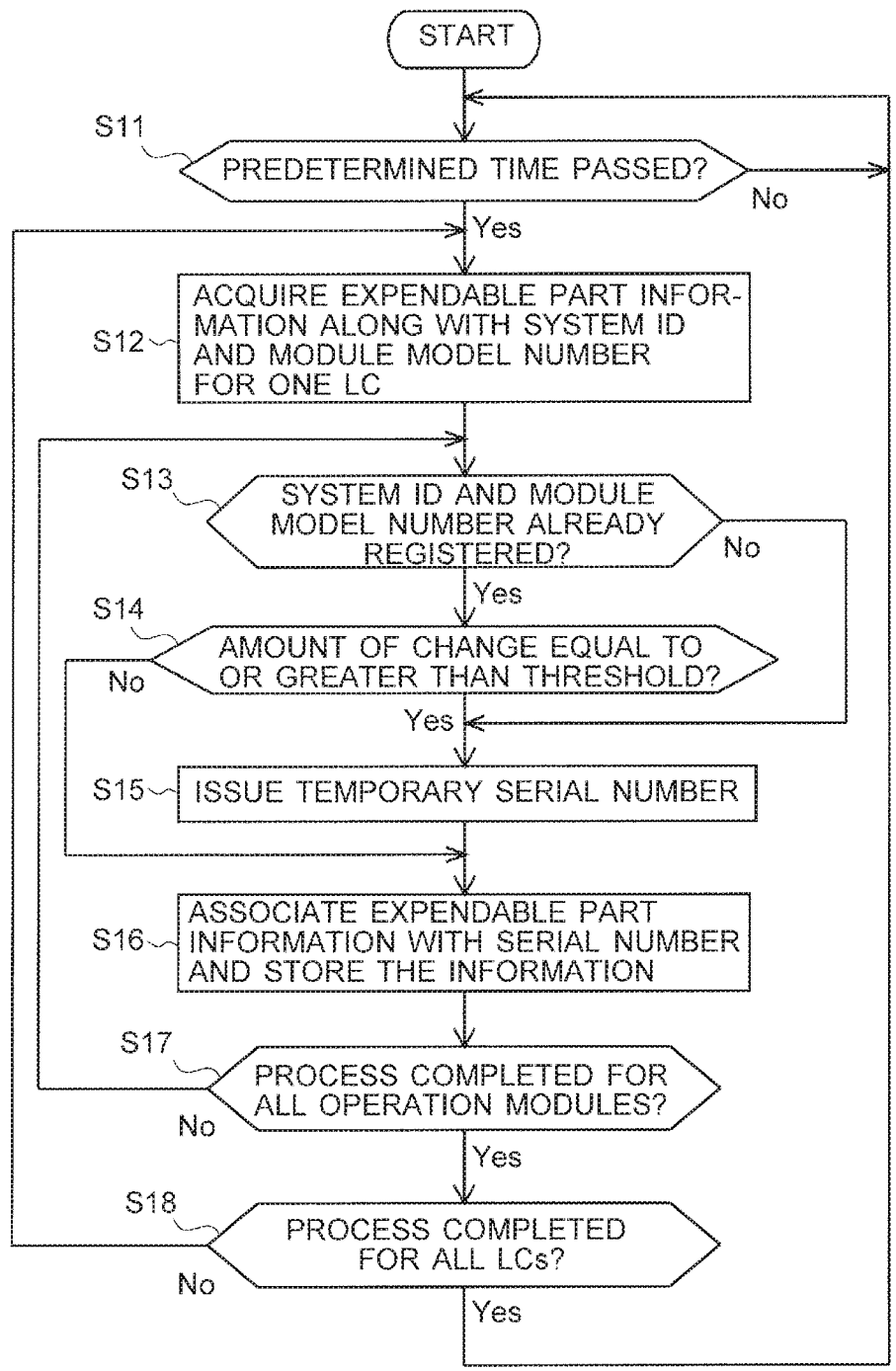
FIG. 3 is a flowchart showing the procedure of the process of updating expandable part information performed by a management program in the embodiment.
Figure 4:
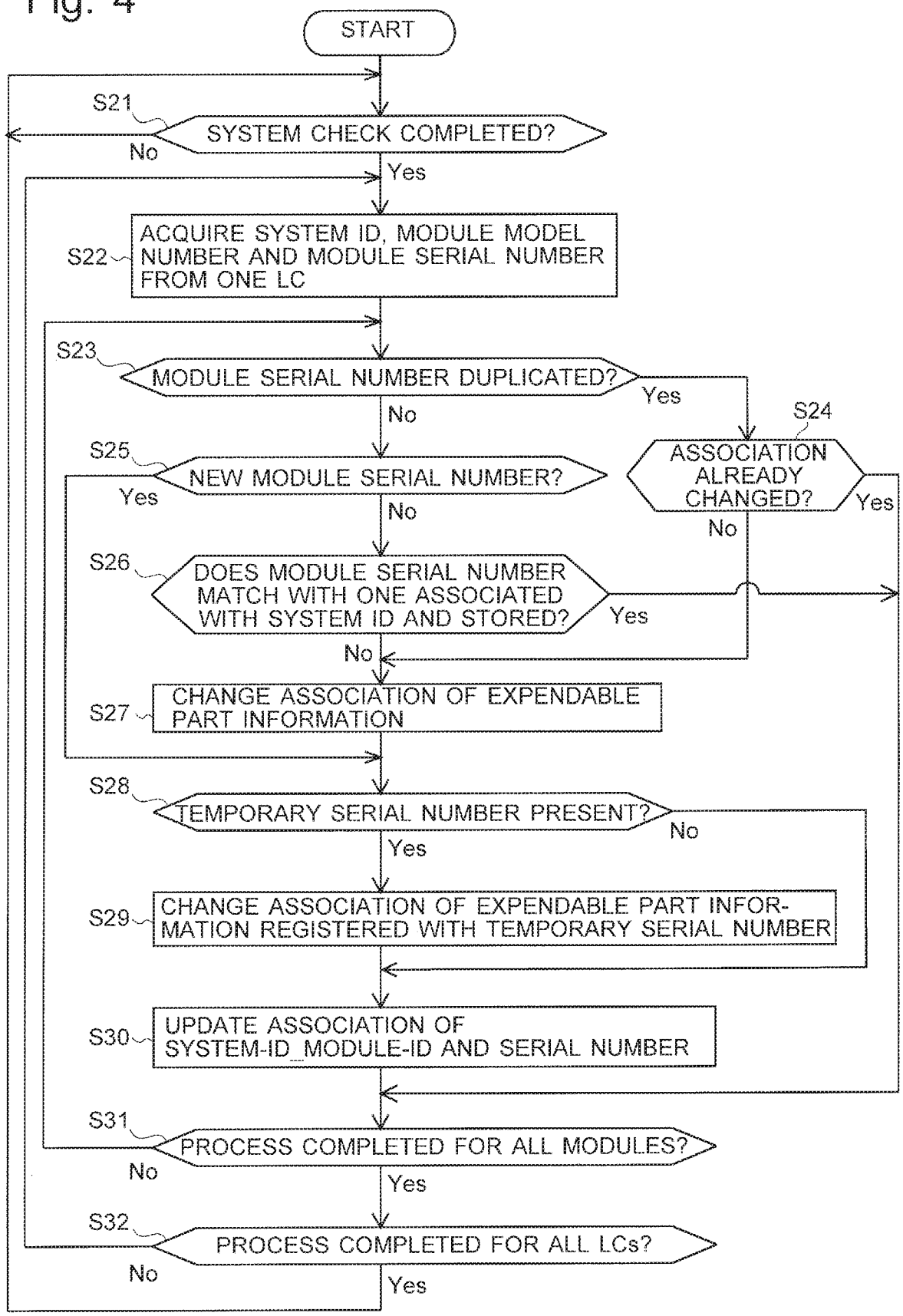
FIG. 4 is a flowchart showing the procedure of the process of updating the module serial number performed by a management program in the embodiment.

An operation of the management system according to the present embodiment is hereinafter described with reference to the flowcharts of FIGS. 3 and 4. The flowcharts show the procedure of the processes performed by the functional blocks realized by the management program installed on the information communication terminal 130. Specifically, FIG. 3 shows the operations in the process of acquiring information on the number of times of use or time of use of each expendable part (this information is hereinafter called the "expendable part information"), while FIG. 4 shows the procedure of the process of acquiring the serial numbers of each operation module. In the following descriptions, the model number of an operation module may be abbreviated as the "module model number".

Similarly, the serial number of an operation module may be abbreviated as the "module serial number".

In the following example, it is assumed that the acquisition of the expendable part information is performed at predetermined intervals of time (e.g. once every hour), while the acquisition of the module serial number is performed immediately after the execution of the system check of each LC (which is normally performed once every day). It should be noted that the timing of the acquisition of the expendable part information and that of the acquisition of the module serial number are not limited to the present example. For example, the expendable part information or module serial number may be acquired upon completion of a specific process, such as a sample analysis in each LC 110*a-c*, or upon entry of a user command into the data processor 116*a-c* or information communication terminal 130.

Initially, the process of updating the expendable part information is described with reference to FIG. 3. The information acquirer 161 determines whether or not a predetermined length of time (e.g. one hour) has passed since the previous acquisition of the expendable part information (Step S11). When it is determined that the predetermined length of time has passed, the information acquirer 161 acquires, from one of the system controllers 115*a-c* (via one of the data processor 116*a-c*), the system ID of the system controller, model numbers of all operation modules connected to the system controller and expendable part information related to the expendable parts included in each of those operation modules (Step S12). In each of the system controllers 115*a-c*, the expendable part information is stored in a memory in the built-in microcontroller of the system controller 115*a-c*.

Subsequently, the temporary serial number assigner 162 accesses the management server 150 via the Internet 140 to determine, for one of the model numbers of the operation modules acquired in Step S12, whether or not the model number is stored in the LC information storage section 152 and associated with the system ID acquired in Step S12 (Step S13).

For example, consider the following situation: In Step S12, the system ID ("SC-1") of the system controller 115*a* as well as the model numbers and the expendable part information related to each of the four modules of the liquid supply unit 111*a*, auto-sampler 112*a*, column oven 113*a* and detector 114*a* are acquired from the system controller 115*a*. Then, in Step S13, it is determined whether or not the model number of the detector 114*a* ("D145S") is associated with the system ID of the system controller 115*a* in the stored information.

In this situation, suppose that the detection unit 114*a* is a unit which has been transferred to the LC 110*a* after the previous execution of the system check, and that its model number is different from that of the detector which was connected to the system controller 115*a* at the point in time of the previous execution of the system check. In this case, the model number "D145S" is not associated with the system ID "SC-1" of the system controller 115*a* in the LC information storage section 152. Therefore, the determination result in Step S13 will be "No".

If the determination result in Step S13 is "No", the temporary serial number assigner 162 issues a temporary serial number (Step S15). The temporary serial number should be different from any of the module serial numbers stored in the LC information storage section 152. Subsequently, the combination of the system ID and the module model number checked in Step S13 is associated with the temporary serial number issued in Step S15 and the expendable part information related to the operation module acquired in Step S12. These pieces of information are transmitted through the Internet 140 to the management server 150, which stores the information in the LC information storage section 152 (Step S16).

For example, in the previously described case, the system ID "SC-1" and the model number "D145S" of the detection unit 114*a* checked in Step S13 will be associated with the temporary serial number issued in Step S15 and the expendable part information related to the detector 114*a* acquired in Step S12, and these pieces of information will be stored in the LC information storage section 152.

On the other hand, in the previously described example, the determination result in Step S13 will be "Yes" if the detection unit 114*a* is a unit which has been transferred to the LC 110*a* after the previous execution of the system check and has the same model number as the detector which was previously connected to the system controller 115*a* (this case is hereinafter called "Case A"), or if the detection unit 114*a* was already connected to the system controller 115*a* at the point in time of the previous execution of the system check (this case is hereinafter called "Case B").

If the determination result in Step S13 is "Yes", the temporary serial number assigner 162 reads, from the LC information storage section 152, the expendable part information associated with the combination of the system ID and the module model number which were checked in Step S13, and compares the read information with the expendable part information related to the detection unit 114*a* acquired in Step S12. Then, it determines whether or not the difference between the two information, i.e. the amount of change in the number of times of use or time of use of each expendable part, is equal to or greater than a predetermined threshold (Step S14).

In Case A, the expendable part information must significantly change from the previous acquisition of the expendable part information, so that the result of Step S14 will be "Yes". In Case B, the expendable part information cannot significantly change from the previous acquisition of the expendable part information, so that the result of Step S14 will be "No".

If the determination result in Step S14 is "Yes", the temporary serial number assigner 162 issues a temporary serial number (Step S15). Subsequently, the combination of the system ID and the module model number checked in Step S13 is associated with the issued temporary serial number and the expendable part information related to the operation module acquired in Step S12. These pieces of information are transmitted through the Internet 140 to the management server 150, which stores the information in the LC information storage section 152 (Step S16).

For example, in Case A, the system ID "SC-1" and the model number "D145S" of the detection unit 114a checked in Step S13 will be associated with the temporary serial number issued in Step S15 and the expendable part information related to the detector 114a acquired in Step S12, and these pieces of information will be stored in the LC information storage section 152.

If the determination result in Step S14 is "No", the information manager 163 writes the expendable part information related to the operation module acquired in Step S12 over the expendable part information associated with the system ID and the model number of the operation module (i.e. the same combination as checked in Step S13) as well as the serial number of the operation module already stored in the LC information storage section 152 (Step S16).

For example, in Case B, the expendable part information related to the detector 114a acquired at the previous acquisition of the expendable part information is already associated with the system ID "SC-1", model number "D145S" of the detection unit 114a, and serial number "d11111" of the detection unit 114a in the stored information. This expendable part information is overwritten with the latest expendable part information related to the detector 114a acquired in Step S12.

Subsequently, the information manager 163 determines whether or not the processes of Steps S13-S16 have been completed for all operation modules whose module model numbers have been acquired in Step S12 (Step S17). If it is determined that those processes have not been completed, the operation returns to Step S13 to perform Steps S13-S16 for one of the remaining operation modules. The processes of Steps S13-S17 are repeatedly performed until the determination result in Step S17 turns to "Yes". After that, the information manager 163 determines whether or not the processes of Steps S12-S17 have been completed for all LCs connected to the information communication terminal 130 (Step S18). If it is determined that those processes have not been completed ("No" in Step S18), the operation returns to Step S12 to repeat the processes of Steps S12-S18 for the remaining LCs. Then, when it is determined that the processes of Steps S12-S17 have been completed for all LCs ("Yes" in Step S18), the operation returns to Step S11.

A process of updating the module serial number is subsequently described with reference to FIG. 4. The information acquirer 161 determines whether or not a system check of any of the LCs 110a, 110b and 110c has been performed (Step S21). When a system check for any of the LCs has been completed, the information acquirer 161 receives the result of the system check transmitted from the LC, and extracts, from the result of the system check, the system ID of the system controller included in the LC as well as the model numbers and serial numbers of all operation modules included in the same LC (Step S22). The module model numbers and module serial numbers are also stored in the memory in the built-in microcontroller of the system controller 115a-c in each of the system controllers 115a-c.

Subsequently, the transfer detector 164 accesses the management server 150 through the Internet 140 and determines, for one of the module serial numbers acquired in Step S22, whether or not the module serial number is stored in the LC information storage section 152 but is associated with a different system ID from the system ID acquired in Step S22 (Step S23).

If the result of Step S23 is "Yes", i.e. if there is a duplication of the module serial number, the transfer detector 164 judges that a transfer of an operation module has performed. Then, the transfer detector 164 determines whether or not the association of the module serial number concerned has been changed since the completion of the previous system check (e.g. within the period from the previous day's system check to the latest system check) (Step S24). If it is determined that such a change has been made (i.e. if "Yes" in Step S24), the operation proceeds to Step S31 (which will be described later).

In Step S24, if it is determined that no change in the association has been made (i.e. if "No" in Step S24), the operation proceeds to Step S27 to change the association of the expendable part information. In this situation, it is reasonable to consider that the module serial number checked in Step S23 has been transferred from the LC related to the "different system ID" mentioned earlier. Accordingly, the information manager 163 changes the association of the expendable part information which is currently associated with the combination of the "different system ID" (i.e. the system ID related to the LC on the giving end of the transfer) and the module serial number in the LC information storage section 152, to the state of being associated with the combination of the system ID acquired in Step S22 (i.e. the system ID of the LC on the receiving end of the transfer) and the serial number of the same type of operation module as the transferred one stored in the LC information storage section 152 (Step S27).

In the above description, if the operation module which has been judged to have been transferred is a liquid supply unit, the "serial number of the same type of operation module as the transferred one" means the serial number of the liquid supply unit associated with the system ID of the LC on the receiving end of the transfer in the LC information storage section 152. If the operation module which has been judged to have been transferred is a detection unit, the aforementioned "serial number" means the serial number of the detection unit associated with the system ID of the LC on the receiving end of the transfer in the LC information storage section 152.

The expendable part information originally associated with the "combination of the system ID of the LC on the receiving end of the transfer and the serial number of the same type of operation module as the transferred one" in the stored information is the information related to an operation module which is not currently connected to the LC on the receiving end of the transfer. Accordingly, this expendable part information should be stored in the unused module information storage section 153 and associated with the module serial number with which the same information was associated.

In Step S23, if it is not determined that there is a duplication of the module serial number (i.e. if "No" in Step S23), the transfer detector 164 determines whether or not the module serial number checked in Step S23 is a number which is stored in neither the LC information storage section 152 nor the unused module information storage section 153 (i.e. whether or not the module serial number is a new one) (Step S25).

If the results of both Steps S23 and S25 have been "No", the operation proceeds to Step S26, where the transfer detector 164 determines whether or not the module serial number checked in Step S23 matches with one of the module serial numbers stored in the LC information storage section 152 and associated with the system ID acquired along with the module serial number concerned in Step S22, or in other words, whether or not the combination of the system ID and the module serial number acquired in Step S22 matches with one of the combinations of the system ID and the module serial number stored in the LC information storage section 152 (Step S26). If it is determined that there is no such matching (i.e. if "No" in Step S26), the operation proceeds to Step S27, where the expendable part information which is currently associated with the module serial number acquired in Step S22 and stored in either the LC information storage section 152 or unused module information storage section 153 is changed to the state of being associated with the same system ID as the one acquired in Step S22 stored in the LC information storage section 152.

In Step S25, if it is determined that the module serial number is a new one (i.e. if "Yes" in Step S25), or if the association of the expendable part information is changed as described earlier after the determination that there is a duplication of the module serial number or after the determination that the combination of the system ID and module serial number does not match with any of the combinations stored in the LC information storage section 152 (i.e. if Step S27 is performed after the result of Step S23 or S26 has been "Yes"), the operation proceeds to Step S28. In Step S28, the information manager 163 determines whether or not there is a temporary serial number stored in the LC information storage section 152 and associated with the combination of the system ID acquired in Step S22 and the model number related to the operation module (acquired in Step S22 and) checked in Steps S23, S25 and S26.

If the result of Step S28 is "Yes", the information manager 163 changes the association of the expendable part information which is associated with the temporary serial number in the stored information (Step S29). As described earlier, the temporary serial number is issued when the process of updating the expendable part information as shown in FIG. 3 is performed after the transfer of an operation module is performed. The system ID associated with the temporary serial number is the system ID on the receiving end of the transfer of the operation module, and the module model number associated with the temporary serial number is the model number of the transferred operation module. Once the model number is known, it is possible to identify the type of operation module (liquid supply unit, auto-sampler, column oven, or detector). Therefore, it is now possible to identify the combination of the LC and the type of operation module to which the expendable part information associated with the temporary serial number should be related (i.e. to which the expendable part information should be assigned). Accordingly, in Step S29, the expendable part information associated with the temporary serial number is changed to the state of being associated with the combination of the system ID, module model number and serial number to which the information should be assigned.

For example, if a temporary serial number (e.g. "x0001") is associated with the system ID "SC-1" and the model number of the detector (e.g. "D145A") of LC 110*a*, the expendable part information associated with this temporary serial number "x0001" is changed to the state of being associated with the system ID "SC-1" of the LC 110*a* as well as the model number (e.g. "D145S") and serial number (e.g. "d0001") related to the detector stored in the LC information storage section 152.

After Step S29 has been completed, or if it is determined in Step S28 that there is no temporary serial number, the information manager 163 updates the association of the system ID and the module serial number (and module model number) in the LC information storage section 152 so that the serial number (and module model number) of the transferred operation module is correctly associated with the system ID of the LC on the receiving end of the transfer (Step S30).

That is to say, at this point in time, although the expendable part information associated with the system ID of the LC on the receiving end of the transfer has already been updated to the information on the currently connected operation module by the execution of Step S27 or S29, the model number and serial number of the operation module associated with the system ID remain unchanged from the state before the transfer. Accordingly, the information manager 163 changes the module model number and module serial number with which the expendable part information updated in Step S27 or S29 is associated in the LC information storage section 152, to the module model number and module serial number acquired in Step S22 (or specifically, the module serial number checked in Step S23 and the module model number acquired in combination with the same module serial number in Step S22).

After Step S30 has been completed, or if it is determined in Step S23 that there is a duplication of the module serial number and it is further determined in Step S24 that the association of the module serial number concerned has already been changed (i.e. if the determination results in both Steps S23 and S24 have been "Yes"), or if it is determined in Step S26 that the combination of the system ID and the module serial number matches with one of the combinations stored in the LC information storage section 152 (i.e. if the determination result in Step S26 is "Yes"), the operation proceeds to Step S31, where the information manager 163 determines whether or not the processes of Steps S23-S30 have been completed for all module serial numbers acquired in Step S22. If the determination result in Step S31 is "No", the operation returns to Step S23 to repeatedly perform the processes of Steps S23-S31 until the determination result in Step S31 turns to "Yes". If the determination result in Step S31 is "Yes", the information manager 163 subsequently determines whether or not the processes of Steps S22-S31 have been completed for all LCs connected to the information communication terminal 130 (Step S32). If the determination result in Step S32 is "No", the operation returns to Step S22 to repeatedly perform the processes of Steps S22-S32 for the remaining LCs. When a determination result of "Yes" is obtained in Step S32, the operation returns to Step S21.

A specific example of the process of updating the module serial number (FIG. 4) is hereinafter described. For example, consider the following situation: As indicated by the thick arrows in FIG. 1, the detection unit 114*a* (with model number "D145S" and serial number "d0001") is removed from the system controller 115*a* (with system ID "SC-1") of the LC 110*a* and transferred to the system controller 115*b* (with system ID "SC-2") of the LC 110*b*. The detection unit 114*b* (with model number "D145S" and serial number "d0002") originally connected to the system controller 115*b* is placed in storage without being connected to any other system controller. The process of updating the expendable part information (FIG. 3) is not performed within the period from the previous transfer of an operation module to the execution of the process of updating the serial number (FIG. 4), and therefore, no temporary serial number is issued.

When the transfer of the detector as just mentioned is performed, the system controller 115*b* of the LC 110*b* on the receiving end of the transfer recognizes the model number "D145S" and serial number "d0001" of the newly connected detector 114*a* and stores those pieces of information in the memory of the built-in microcontroller of the system controller 115*b* (although the serial numbers of the operation modules other than the detection unit are also recognized at this point, descriptions of those other serial numbers will be omitted). Now, no detection unit is connected to the system controller 115*a* of the LC 110*a* on the giving end of the transfer. However, the system controller 115*a* cannot distinguish this state from the state where a detection unit is connected but is not energized. Accordingly, the model number "D145S" and serial number "d0001" of the detector 114*a* stored in the memory of the built-in microcontroller of the system controller 115*s* are still retained even after the transfer.

Subsequently, the process of updating the module serial number (FIG. 4) is performed: Suppose that Steps S22-S31 are initially performed for the LC 110*a* from which the detection unit 114*a* has been transferred. In this case, the system ID "SC-1", model number "D145S" of the detection unit 114*a*, and serial number "d0001" of the detection unit 114*a* are acquired by the information acquirer 161 in Step S22. In the LC information storage section 152 at this point, the serial number "d0001" of the detection unit 114*a* is associated with only the system ID "SC-1" of the LC 110*a* on the giving end of the transfer. Accordingly, it is determined in Step S23 that there is no duplication of the serial number. Therefore, neither the process of changing the association of the expendable part information (Steps S27 and S29) nor the process of changing the association of the module serial number (Step S30) is carried out, and the operation returns to Step S22 via Step S32.

Subsequently, when Steps S22-S31 are performed for the LC 110*b* to which the detection unit 114*a* has been transferred, the system ID "SC-2", model number "D145S" of the detection unit 114*a*, and serial number "d0001" of the detection unit 114*a* are acquired by the information acquirer 161 in Step S22. In the LC information storage section 152 at this point, the serial number "d0001" of the detection unit 114*a* is associated with the system ID "SC-1" of the LC 110*a* on the giving end of the transfer. Accordingly, it is determined in Step S23 that there is a duplication of the serial number. Additionally, since the association concerning this module serial number is not changed yet, the determination result in Step S24 is "No", so that the operation proceeds to Step S27 to change the association of the expendable part information. Specifically, the expendable part information related to the detection unit 114*a* which has been associated with the combination of the system ID of the LC 110*a*, model number of the detection unit 114*a*, and serial number of the detection unit 114*a* (i.e. "SC-1_D145S_d0001") in the LC information storage section 152 (this information is hereinafter called the "expendable part information a") is changed to the state of being associated with the combination of the system ID of the LC 110*b*, model number of the detection unit 114*b*, and serial number of the detection unit 114*b* (i.e. "SC-2_D145S_d0002") by the information manager 163.

The expendable part information originally associated with "SC-2_D145S_d0002", i.e. the expendable part information related to the detection unit 114*b* which has been removed (this information is hereinafter called the "expendable part information b"), is associated with the combination of the model number and serial number of the detection unit 114*b* (i.e. "D145S_d0002") and stored in the unused module information storage section 153.

At the point of completion of the previously described processes, only the expendable part information of the transferred detection unit 114*a* is updated to the state of being associated with the system ID of the LC 110*b*. The model number and serial number of the detection unit 114*a* are still associated with the system ID "SC-1" of the LC 110*a* from which the same unit has been transferred. Furthermore, although the expendable part information of the detection unit 114*b* removed from the LC 110*b* has been moved to the unused module information storage section 153, the model number and serial number of the detection unit 114*b* are still associated with the system ID "SC-2" of the LC 110*b*.

Accordingly, in Step S30, the information manager 163 changes the module model number and module serial number in each of the two combinations of "SC-1_D145S_d0001 (no expendable part information)" and "SC-2_D145S_d0002 expendable part information a" stored in the LC information storage section 152, to "SC-1_(no module model number)_(no module serial number)_(no expendable part information)" and "SC-2_D145S_d0001_expendable part information a", respectively.

Another case is hereinafter described: The transfer of the detection unit is similarly performed as indicated by the thick arrows in FIG. 1, but Steps S22-S31 in the subsequent process of updating the module serial number (FIG. 4) are initially performed for the LC 110*b* to which the detection unit 114*a* has been transferred. As in the previously described case, no temporary serial number is issued. In the present case, the system ID "SC-2", model number "D145S" of the detection unit 114*a*, and serial number "d0001" of the detection unit 114*a* are acquired by the information acquirer 161 in Step S22. In the LC information storage section 152 at this point, the serial number "d0001" of the detection unit 114*a* is associated with the system ID "SC-1" of the LC 110*a* on the giving end of the transfer. Accordingly, it is determined in Step S23 that there is a duplication of the serial number. Additionally, since the association concerning this serial number is not changed yet, the determination result in Step S24 is "No", so that the operation proceeds to Step S27 to change the association of the expendable part information. Specifically, the "expendable part information a" associated with "SC-1_D145S_d0001" in the LC information storage section 152 is changed to the state of being associated with "SC-2_D145S_d0002". Meanwhile, the "expendable part information b" originally associated with "SC-2_D145S_d0002" is associated with "D145S_d0002" and stored in the unused module information storage section 153. Furthermore, in the subsequent Step S30, the model number and serial number in each of the two combinations of "SC-1_D145S_d0001 (no expendable part information)"

and "SC-2_D145S_d0002 expendable part information a" stored in the LC information storage section 152 are respectively changed to "SC-1_(no module model number)_(no module serial number)_(no expendable part information)" and "SC-2_D145S_d0001_expendable part information a".

Subsequently, when Steps S22-S31 in FIG. 4 are performed for the LC 110a from which the detection unit 114a has been transferred, the system ID "SC-1", model number "D145S" of the detection unit 114a, and serial number "d0001" of the detection unit 114a are acquired in Step S22. In the LC information storage section 152 at this point, the serial number "d0001" of the detection unit 114a is associated with the system ID "SC-2" of the LC 110b on the receiving end of the transfer, as just described. Accordingly, it is determined in Step S23 that there is a duplication of the serial number. However, the association of this serial number "d0001" has already been updated by the process of Steps S30 performed for the LC 110b on the receiving end of the transfer. Therefore, the determination result in Step S24 is "Yes", and the operation proceeds to Step S31 without making a change to the association.

Hereinafter described is another example, in which the detection unit 114a (with model number "D145S" and serial number "d0001") connected to the system controller 115a of the LC 110a and the detection unit 114b (with model number "D145S" and serial number "d0002") connected to the system controller 115b of the LC 110b are exchanged, as indicated by the thick dashed arrow in FIG. 1. Similar to the previously described example, no temporary serial number is issued. Under these conditions, suppose that the process of updating the module serial number (FIG. 4) is performed after the exchange of the aforementioned units, and Steps S22-S31 are initially performed for the LC 110a. In this case, the system ID "SC-1", model number "D145S" of the detection unit 114b, and serial number "d0002" of the detection unit 114b are acquired by the information acquirer 161 in Step S22. In the LC information storage section 152 at this point, the serial number "d0002" is associated with the system ID "SC-2" of the LC 110b on the giving end of the transfer. Accordingly, it is determined in Step S23 that there is a duplication of the serial number. Additionally, since the association concerning this serial number is not changed yet, the determination result in Step S24 is "No". Accordingly, the operation proceeds to Step S27, where the "expendable part information b" associated with "SC-2_D145S_d0002" in the LC information storage section 152 is changed to the state of being associated with "SC-1_D145S_d0001". Meanwhile, the expendable part information originally associated with "SC-1_D145S_d0001", i.e. the "expendable part information a" of the detection unit 114a, is associated with the combination of the model number and serial number of the same detection unit 114a (i.e. "D145S_d0001") and temporarily stored in the unused module information storage section 153. Furthermore, in Step S30, the model number and serial number in each of the two combinations of "SC-1_D145S_d0001_expendable part information b" and "SC-2_D145S_d0002 (no expendable part information)" stored in the LC information storage section 152 are respectively changed to "SC-1_D145S_d0002 expendable part information b" and "SC-2 (no module model number)_(no module serial number)_(no expendable part information)".

Next, when Step S22 is performed for the LC 110b, the system ID "SC-2", model number "D145S" of the detection unit 114a, and serial number "d0001" of the detection unit 114a are acquired. This serial number "d0001" is not associated with any system ID in the LC information storage section 152 at this point. Therefore, it is determined in Step S23 that there is no duplication of the serial number (i.e. "No" in Step S23). Furthermore, since the serial number "d0001" is stored in the unused module information storage section 153, it is determined in Step S25 that this serial number is not a new one (i.e. "No" in Step S25). Additionally, since the serial number "d0001" is not a serial number associated with the system ID "SC-2" acquired in Step S22 in the LC information storage section 152, the determination result in Step S26 is also "No". As a result, the operation proceeds to Step S27 to change the association of the expendable part information, and further to Step S30 to change the association of the module model number and module serial number. Specifically, the "expendable part information a", which has been associated with "D145S_d0001" (i.e. the combination of the model number and serial number of the detection unit 114a) and stored in the unused module information storage section 153, is associated with the system ID "SC-2" stored in the LC information storage section 152 in Step S25, and furthermore, the model number "D145S" and serial number "d0001" of the detector 114a are associated with the same system ID. As a result, the combination which has been stored in the LC information storage section 152 for the LC 110b, i.e. "SC-2 (no module model number)_(no module serial number)_(no expendable part information)", is changed to "SC-2_D145S_d0001_expendable part information a".

Hereinafter described is still another example, in which the detection unit 114a (with model number "D145S" and serial number "d0001") is removed from the system controller 115a of the LC 110a and replaced by a new detection unit (with model number "D145S" and serial number "d0004") which has not been connected to any of the system controllers 115a-c. For the following description, it is assumed that the process of updating the expendable part information (FIG. 3) has been performed within the period from the aforementioned transfer to the execution of the process of updating the serial number (FIG. 4), with the result that the expendable part information related to the new detection unit (which is hereinafter called the "expendable part information c") is associated with the combination of the system ID "SC-1" of the LC 110a, model number "D145S" of the new detection unit, and temporary serial number ("x0001"), i.e. "SC-1_D145S_x0001, and is stored in the LC information storage section 152. In this situation, when Step S22 in FIG. 4 is performed for the LC 110a, the system ID "SC-1", model number "D145S" of the new detection unit, and serial number "d0004" of the same detection unit are acquired by the information acquirer 161. Since this new detection unit was not connected to any of the LCs 110a, 110b and 110c at the time of the previous system check, the serial number "d0004" is stored in neither the LC information storage section 152 nor the unused module information storage section 153. Therefore, it is determined in Step S23 that there is no duplication of the serial number, and in the subsequent Step S25, it is determined that "d0004" is a new module serial number. Then, in Step S28, it is determined that there is a temporary serial number, and the operation proceeds to Step S29, where the "expendable part information c" which has been associated with the combination of the system ID of the LC 110a, model number of the new detection unit and temporary serial number, i.e. "SC-1_D145S_x0001", is made to be associated with "SC-1_D145S_d0001" stored in the LC information storage section 152. Meanwhile, the "expendable part information a" related to the detection unit 114a which was originally associated with "SC-1_D145S_d0001" is associated with the combination of the model number and serial number of the detection unit 114a, i.e. "D145S_d0001", and stored in the unused module information storage section 153. Furthermore, in Step S30, the module model number and module serial number included in the combination of "SC-1_D145S_d0001_expendable part information c" stored in the LC information storage section 152 are updated with those acquired in Step S22, to "SC-1_D145S_d0004 expendable part information c".

Figure 5:
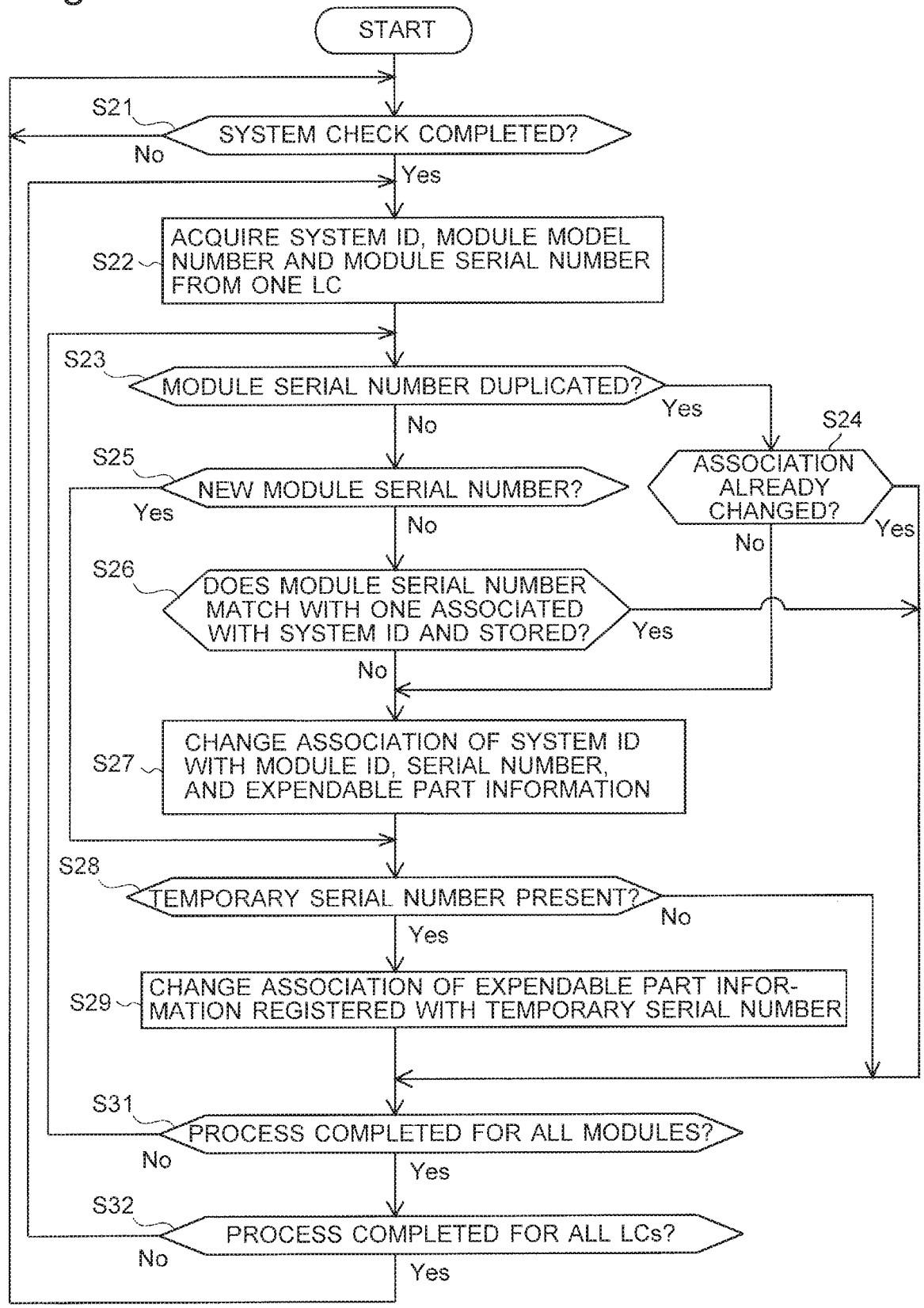
FIG. 5 is a flowchart showing another example of the procedure of the process of updating the module serial number.

In any of the previously described examples, the association of the module serial number (and module model number is changed in Step S30 after the association of the expendable part information is changed in Step S27 or S29. Alternatively, as shown in FIG. 5, the association of the module serial number (and module model number may be changed in Step S27 in addition to the expendable part information. In this case, after the associations have been changed in Step S27, the operation proceeds to Step S28 to determine whether or not a temporary serial number is stored in the LC information storage section 152. If it is determined in Step S28 that a temporary serial number is stored (i.e. if "Yes" in Step S28), the operation proceeds to Step S29 to change the association of the expendable part information associated with the temporary serial number in the stored information, and subsequently proceeds to Step S31. If it is determined in Step S28 that no temporary serial number is stored (i.e. if "No" in Step S28), the operation proceeds to Step S31, bypassing Step S29. The other processes are the same as in the flowchart of FIG. 4.

In the case of removing an operation module from one of the LCs and discarding it, the user manually enters a command for discarding into the data processor 116b or information communication terminal 130 (e.g. by pressing a "Delete" button displayed on a monitor, using the mouse or similar operation device) or connects the operation module to be discarded to a system controller for discarding (not shown) which is connected to the information communication terminal 130 via the LAN 120. From this operation, the information manager 163 recognizes that the operation module should be discarded and stores the combination the model number and serial number of the same operation module as well as the expendable part information associated with that combination into the discarded module information storage section 154. After that, it deletes those pieces of information from the LC information storage section 152.

In any of the previously described examples, the process of updating the module serial number is sequentially performed for each of the LCs connected to the information communication terminal 130. The processing procedure in the present invention is not limited to such a form. For example, at the point in time where the information acquirer 161 has received the results of the system check from the system controllers of all LCs, the information manager 163 may determine whether or not there is an inconsistency between the combinations of the system ID and module serial number included in the system-check results, and the combinations of the system ID and module serial number associated with each other in the LC information storage section 152. If there is a discrepancy, it is possible to determine that a transfer of an operation module has occurred. If it is determined that a transfer has occurred, the combinations of the system ID and module serial number stored in the LC information storage section 152 should be changed to the combinations included in the system-check results. Furthermore, according to this change, the association of the expendable part information stored in the LC information storage section 152 or unused module information storage section 153 should also be changed.

As noted earlier, in the conventional analyzing device management system, the operation modules connected to each system controller are recognized based on their respective model numbers. Therefore, when a rearrangement of the operation modules, such as the transfer of an operation module from one analyzing device to another one, exchange (transposition) of operation modules between two analyzing devices, or installation of a new operation module in an analyzing device has been performed, it is impossible for the management system to detect the rearrangement if there is no change in the model numbers of the operation modules before and after the rearrangement. By comparison, in the analyzing device management system according to the previously described embodiment, the operation modules connected to each system controller are recognized based on their respective serial numbers. Therefore, even if there is no change in the model numbers of the operation modules before and after the rearrangement of the operation modules, the system can detect the rearrangement and appropriately manage the expendable part information related to each operation module.

Figure 6:
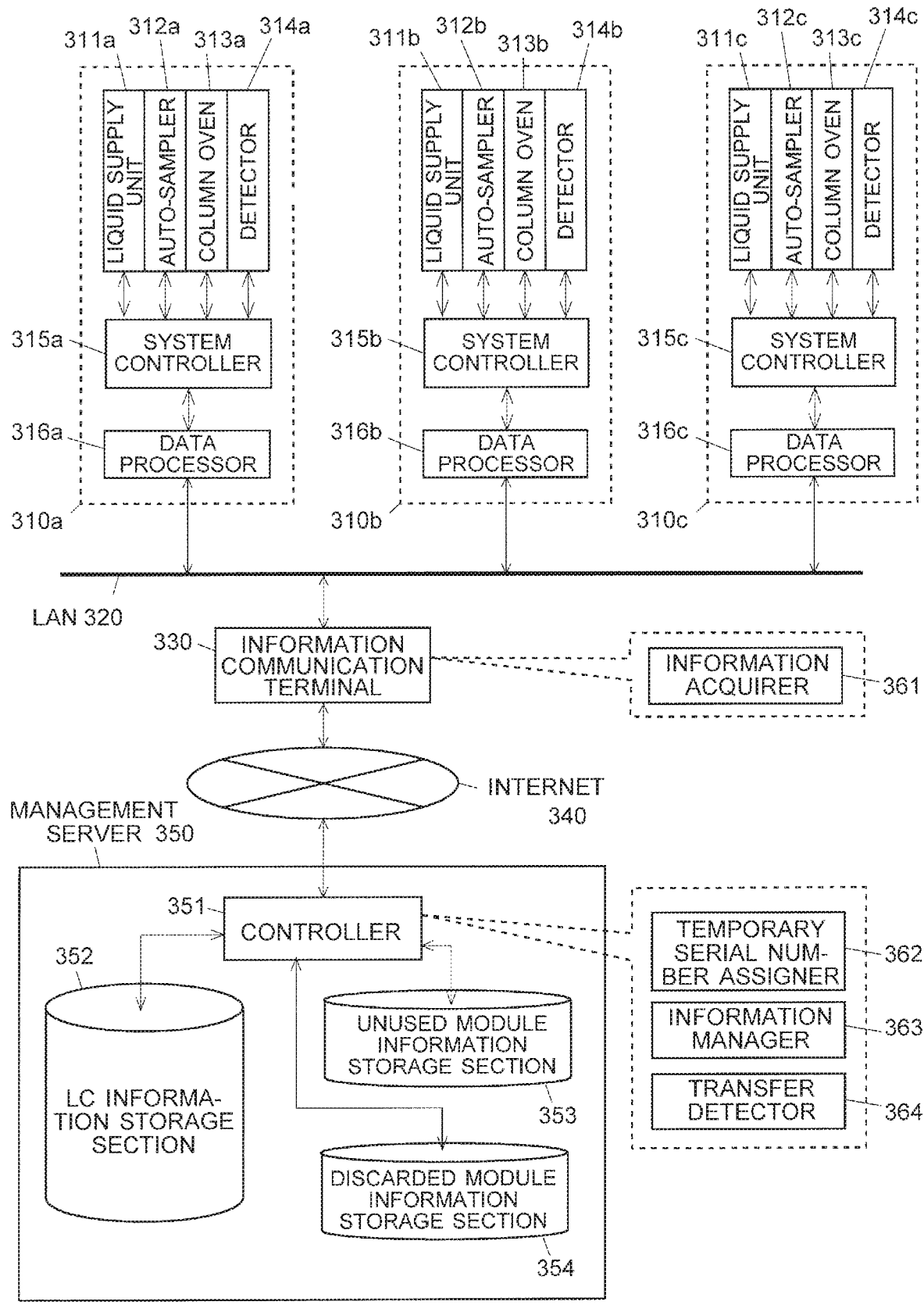
FIG. 6 is a model diagram showing an analyzing device management system according to another embodiment of the present invention.
Figure 7:
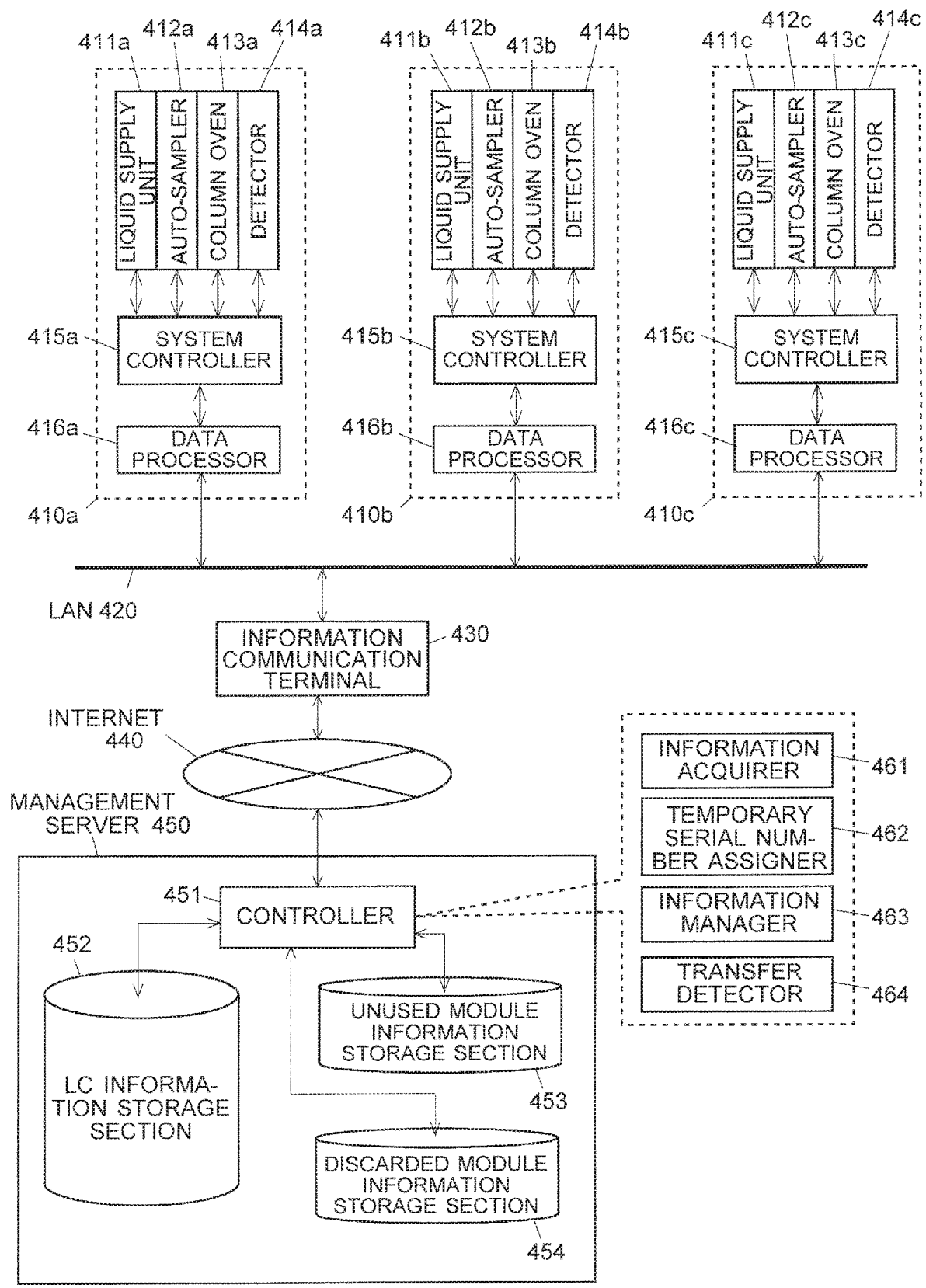
FIG. 7 is a model diagram showing an analyzing device management system according to still another embodiment of the present invention.
Figure 8:
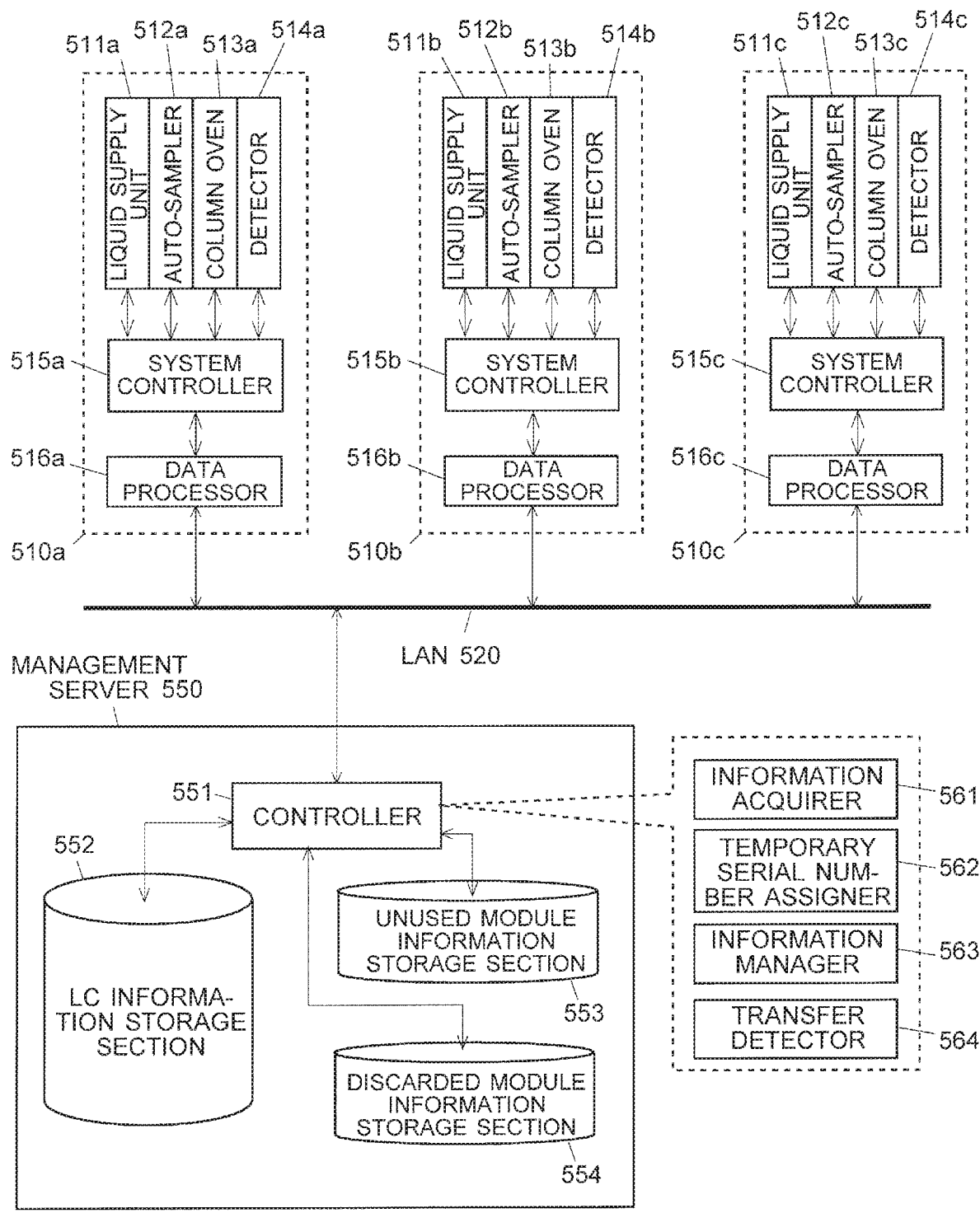
FIG. 8 is a model diagram showing an analyzing device management system according to a different embodiment of the present invention.

Modes for carrying out the present invention have been described thus far using the embodiment. The present invention is not limited to the previous embodiment. Appropriate changes may be made within the spirit of the present invention. For example, in the previous embodiment, the information communication terminal 130 fulfills the functions as the information acquirer 161, temporary serial number assigner 162, information manager 163 and transfer detector 164, as shown in FIG. 1. This may be changed, for example, as shown in FIG. 6, in which those functions are divided up between the information communication terminal 330 and the controller 351 in the management server 350. In the example of FIG. 6, the information communication terminal 330 fulfills the function as the information acquirer 361, while the controller 351 in the management server 350 fulfills the functions as the temporary serial number assigner 362, information manager 363 and transfer detector 364. The division of the functions is not limited to this example. FIG. 7 shows another possible configuration, in which all functional blocks are realized on the controller 451 in the management server 450. FIG. 8 shows still another possible configuration, in which the management server 550 is placed in the same facility as the LC 510a-c, rather than on the Internet, and the management server 550 and the LCs 510a-c are connected to each other via the LAN 520. In this case, the controller 551 in the management server 550 may be configured to fulfill all functions as the information acquirer 561, temporary serial number assigner 562, information manager 563 and transfer detector 564, as shown in FIG. 8, without providing an information communication terminal as used in the first embodiment. It is also possible to provide an information communication terminal as used in the first embodiment between the management server 550 and the LAN 520, in which case all roles of the functional blocks 561-564 may be fulfilled by this information communication terminal, or the roles of the functional blocks 561-564 may be divided up between the information communication terminal and the controller 551 in the management server 550. It should be noted that the components in FIGS. 6-8 which are identical or correspond to the components shown in FIG. 1 are denoted by numerals whose last two digits are the same as those used in FIG. 1.

In the display screen of FIG. 2, only the heater is shown as an expendable part related to the column oven. It is also possible, for example, to include the column to be installed in the column oven as an expendable part related to the column oven. In that case, the management system can acquire the unique identifier of the column with the help of a user who manually enters the identifier into the data processor of the LC or the information communication terminal, or a column oven which automatically reads the unique identifier of the column from a wireless or wired IC chip attached to the column. The unique identifier of the column acquired in this manner, as well as the number of times of use, time of use, pressure and other kinds of information concerning the column which will be acquired later with a predetermined timing, will be included in the expendable part information related to the column oven and stored in the LC information storage section, being associated with the system ID of the system controller to which the column oven concerned is connected.

REFERENCE SIGNS LIST 110a, 110b, 110c . . . Liquid Chromatograph (LC)
111a, 111b, 111c . . . Liquid Supply Unit
112a, 112b, 112c . . . Auto-sampler
113a, 113b, 113c . . . Column Oven
114a, 114b, 114c . . . Detection Unit
115a, 115b, 115c . . . System Controller
116a, 116b, 116c . . . Data Processor
120 . . . Local Area Network (LAN)
130 . . . Information Communication Terminal
161 . . . Information Acquirer
162 . . . Temporary Serial Number Assigner
163 . . . Information Manager
164 . . . Transfer Detector
140 . . . Internet
150 . . . Management Server
151 . . . Controller
152 . . . LC Information Storage Section
153 . . . Unused Module Information Storage Section
154 . . . Discarded Module Information Storage Section

The invention claimed is:

1. An analyzing device management system for managing a plurality of analyzing devices that perform chemical or physical analyses of samples, each analyzing device including a plurality of operation modules and a system controller which performs a general control of the operation modules, each of the plurality of operation modules respectively including an expendable part, the analyzing device management system comprising:
a communication terminal configured to
repeatedly acquire, from the system controller included in each of the analyzing devices, at a previously determined first timing, module identifiers, each of the module identifiers being unique to an individual operation module of the operation modules connected to the system controller; and
repeatedly acquire, from the system controller included in each of the analyzing devices, at a previously determined second timing, information concerning a use history of the expendable part included in each of the operation modules connected to the system controller; and
an information storage configured to store the module identifiers acquired at the first timing, the each stored module identifier being associated with a system control identifier, the system control identifier identifying the system controller to which the operation module corresponding to the module identifier is connected, and to store the information concerning a use history of the expendable part acquired at the second timing, the information concerning the use history being associated with the system control identifier of the system controller to which the operation module including the expendable part is connected;
wherein the communication terminal is further configured to
detect a transfer of an operation module of the plurality of operation modules from one of the plurality of analyzing devices to another one of the plurality of analyzing devices, based on the module identifier associated with the system control identifier of each system controller and stored in the information storage; and
change an association of the module identifier of a transferred operation module and the information concerning the use history of the expendable part included in the transferred operation module, stored in the information storage, from a state of being associated with the system control identifier of the system controller on a giving end of the transfer, to a state of being associated with the system control identifier of the system controller on a receiving end of the transfer, when the transfer of the operation module is detected.

2. The analyzing device management system according to claim 1, wherein:
the communication terminal further configured to judge that a transfer of an operation module has occurred, if the module identifier related to an operation module connected to the system controller of one of the plurality of analyzing devices is already associated with the identifier of another system controller and stored in the information storage at a point in time where the module identifier concerned is acquired from the system controller concerned.

3. The analyzing device management system according to claim 2, wherein:
the communication terminal is further configured to judge that a transfer of a new operation module to the system controller has occurred in one of the plurality of analyzing devices, if the module identifier related to an operation module connected to the system controller concerned is a new module identifier which is not related to the system control identifier of any system controller in the information storage at the point in time where the module identifier concerned is acquired from the system controller concerned; and
the communication terminal is further configured to store a new module identifier of a new operation module in the information storage, if it is judged that a transfer of the new operation module has occurred, the new module identifier being associated with the system control identifier of a system controller for which it has been judged that the transfer of the new operation module has occurred.

4. The analyzing device management system according to claim 3, the communication terminal is further configured to determine, at a point in time where the information concerning the use history of an expendable part included in one of the plurality of operation modules is acquired, an amount of change of the acquired information from the information concerning the use history of the same expendable part stored in the information storage, and for associating the information concerning the use history of the expendable part at the aforementioned point in time and the subsequently obtained information concerning the use history of the expendable part with a temporary module identifier different from the module identifier of any of the operation modules and storing the information in the information storage, if the aforementioned change is equal to or greater than a predetermined threshold, wherein:
after an operation of storing the information concerning the use history of the expendable part associated with the temporary module identifier is initiated in the information storage, when a transfer of an operation module is detected, the communication terminal changes an association of the information concerning the use history of the expendable part associated with the temporary module identifier and stored in the information storage, to a state of being associated with the system control identifier of the system controller on the receiving end of the transfer.

5. The analyzing device management system according to claim 2, wherein the communication terminal is further configured to determine, at a point in time where the information concerning the use history of an expendable part included in one of the plurality of operation modules is acquired, an amount of change of the acquired information from the information concerning the use history of the same expendable part stored in the information storage, and for associating the information concerning the use history of the expendable part at the aforementioned point in time and the subsequently obtained information concerning the use history of the expendable part with a temporary module identifier different from the module identifier of any of the operation modules and storing the information in the information storage, if the aforementioned change is equal to or greater than a predetermined threshold, wherein:
after an operation of storing the information concerning the use history of the expendable part associated with the temporary module identifier is initiated in the information storage, when a transfer of an operation module is detected, the communication terminal changes an association of the information concerning the use history of the expendable part associated with the temporary module identifier and stored in the information storage, to a state of being associated with the system control identifier of the system controller on the receiving end of the predicting the timing for the replacement of each expendable part and showing it to the user based on the information concerning the use history of the expendable part included in the operation module transfer.

6. The analyzing device management system according to claim 1, wherein the communication terminal is further configured to determine, at a point in time where the information concerning the use history of an expendable part included in one of the plurality of operation modules is acquired, an amount of change of the acquired information from the information concerning the use history of the same expendable part stored in the information storage, and for associating the information concerning the use history of the expendable part at the aforementioned point in time and the subsequently obtained information concerning the use history of the expendable part with a temporary module identifier different from the module identifier of any of the operation modules and storing the information in the information storage, if the aforementioned change is equal to or greater than a predetermined threshold, wherein:
after an operation of storing the information concerning the use history of the expendable part associated with the temporary module identifier is initiated in the information storage, when a transfer of an operation module is detected, the communication terminal changes an association of the information concerning the use history of the expendable part associated with the temporary module identifier and stored in the information storage, to a state of being associated with the system control identifier of the system controller on the receiving end of the transfer.

7. The analyzing device management system according to claim 1, wherein the communication terminal is further configured to predict a timing for replacement of each of the expendable parts included in the operation modules and to show the timing to a user based on the information concerning the use history of the expendable parts.

8. The analyzing device management system according to claim 1, wherein the plurality of analyzing devices that perform chemical or physical analyses of samples are chromatographs.

9. The analyzing device management system according to claim 8, wherein the chromatographs are liquid chromatographs.

10. An analyzing device management method for managing a plurality of analyzing devices that perform chemical or physical analyses of samples, each analyzing device including a plurality of operation modules and a system controller which performs a general control of the operation modules, each of the plurality of operation modules respectively including an expendable part, the method comprising:

a) repeatedly acquiring, from the system controller included in each of the analyzing devices, at a previously determined first timing, module identifiers, each of the module identifiers being unique to an individual operation module of the operation modules connected to the system controller;

b) repeatedly acquiring, from the system controller included in each of the analyzing devices, at a previously determined second timing, information concerning a use history of the expendable part included in each of the operation modules connected to the system controller;

c) storing the module identifiers acquired at the first timing in an information storage, the each stored module identifier being associated with a system control identifier, the system control identifier identifying the system controller to which the operation module corresponding to the module identifier is connected, as well as storing the information concerning a use history of an expendable part acquired at the second timing in the information storage, the stored information concerning the use history of the expendable part being associated with the system control identifier of the system controller to which the operation module including the expendable part is connected;

d) determining whether or not a transfer of an operation module of the plurality of operation modules from one of the plurality of analyzing devices to another one of the plurality of analyzing devices has been performed, based on the module identifier associated with the system control identifier of each system controller and stored in the information storage; and e) changing an association of the module identifier of a transferred operation module and the information concerning the use history of the expendable part included in the transferred operation module, stored in the information storage, from a state of being associated with the system control identifier of the system controller on a giving end of the transfer, to a state of being associated with the system control identifier of the system controller on a receiving end of the transfer, when it is determined that the transfer of the operation module has been performed.

11. The analyzing device management method according to claim 10, further comprising predicting a timing for replacement of each of the expendable parts included in the operation modules and showing the timing to a user based on the information concerning the use history of the expendable parts.

12. The analyzing device management method according to claim 10, wherein the plurality of analyzing devices that perform chemical or physical analyses of samples are chromatographs.

13. The analyzing device management method according to claim 12, wherein the chromatographs are liquid chromatographs.

* * * * *